United States Patent [19]

Johansen et al.

[11] Patent Number: 4,888,981
[45] Date of Patent: Dec. 26, 1989

[54] APPARATUS FOR TESTING OF FLUIDS

[76] Inventors: Edgar Johansen, Hjalmar Haalkesv. 4, N-7000 Trondheim, Norway; Hans K. Johnsen, Dybdahlsv. 9a, N-7000 Trondheim, Norway

[21] Appl. No.: 807,902

[22] Filed: Dec. 11, 1985

[30] Foreign Application Priority Data

Dec. 12, 1984 [NO] Norway .................................. 844970

[51] Int. Cl.$^4$ ............................................ G01N 37/00
[52] U.S. Cl. ..................................................... 73/60.1
[58] Field of Search ................................ 73/60.1, 61.4

[56] References Cited

U.S. PATENT DOCUMENTS 3,679,367  7/1972  Negersmith et al. ............ 73/61.4 X

FOREIGN PATENT DOCUMENTS 893720  10/1953  Fed. Rep. of Germany ....... 73/61.4
481815  10/1975  U.S.S.R. ................................. 73/61.4

Primary Examiner—Stewart J. Levy
Assistant Examiner—Joseph W. Roskos
Attorney, Agent, or Firm—Townsend & Townsend

[57] ABSTRACT

Apparatus for testing fluids, especially for testing physical characteristics or susceptibility to process fluids. A rotor (11) includes at least one arced pipe segment (18-21) that can transport the fluid, which is to be tested, and retrieve it during rotation. The pipe segment or segments are preferably connected by adjacent valves.

4 Claims, 4 Drawing Sheets

APPARATUS FOR TESTING OF FLUIDS

When a medium comes in contact with another medium in a closed system, for example, in a processing system, a chemical reaction can occur between them. Other non-chemical reactions can also occur. For example, foam is created by putting soap and water into an agitator.

Oil production systems will often have problems with reactions of this type; this especially applies to foam and emulsion. Foam is a dispersion of gas in liquid whereas emulsion is a dispersion of liquid in liquid. These gases and liquids have been stored in a reservoir where they come in chemical contact with one another. The process that creates emulsion or foam formation is due to the fact that when energy is converted from production and/or transport of the fluids takes place, they are exposed to remixing and turbulence. As formation of such products often produce consequences for the physical development of the processing plant as well as the chemicals to be used, it is desirable to survey such conditions before plant construction begins.

The chemical elements that are present to stablilze foam and emulsions are typical trace elements and can have quite different natures and makeup. Therefore, no one can be found at present with a general background in chemical analysis who can take a given set of fluids and forsee what would happen to this in a given physical environment, such as a processing plant. It has been standard practice to take samples of reservoir fluids and agitate or splash them together and see if foam or emulsion is produced. One has no reliable way, however, to relate the experiments to the actual process because one doesn't have a clear scale of criteria between the laboratory experiments and the process itself. As an example of this, one can cite the problems of deciding container size, agitator speed and agitator time in order to simulate the turbulence inside a given pipe where a constant flow moves along a certain length.

This results in the fact that we can document as to what extent the possibility for foam/emulsion is present, but not if foam/emulsion will be formed in a given situation.

One condition that further complicates the problem is that it is often desirable to find an answer as to possible susceptibility to foam/emulsion formation at the earliest possible stage after an oil field has been discovered. At this stage we have a very limited amount of samples from the field. It can be a matter of a few hundred liters, which will be used for a large number of experiments. This means that one must work with only a small amount of fluids in the apparatuses.

In concern for the scaling and the environment, pumps should not be utilized, as this would be an unknown element in the actual process.

Thus the main goal of this invention is to create an apparatus for testing the various physical properties of process fluids, especially the testing of susceptibility to foam and emulsion formation. To be sure, the aim is to create an apparatus that can physically simulate the various influences that are expected in a certain process, such as pipe flow, one and two-phase flow through jets and shower of oil, water and gas on an oil layer with water below it.

The apparatus should also be able to be used for the selection of the physical and/or chemical remedies that will be used to eliminate a foam problem.

In referring to the invention, this goal can, to a large degree, be accomplished with the help of an apparatus in accordance with that characterized in claim 1.

An important advantage with this apparatus is that the transport of the fluid from apparatus to apparatus under testing, which could disturb sensitive chemical balances, becomes redundant.

The apparatus makes it possible to give the test fluids correct physical treatment, correct physical environment, correct sequence and correct exit fluids for each stage of influence. One can carry out this under the right pressure and temperature with the aid of proper supplementary equipment.

Further advantages of the invention are mentioned in the subclaims.

The invention is described in more detail below with reference to the drawings.

Figure 1:
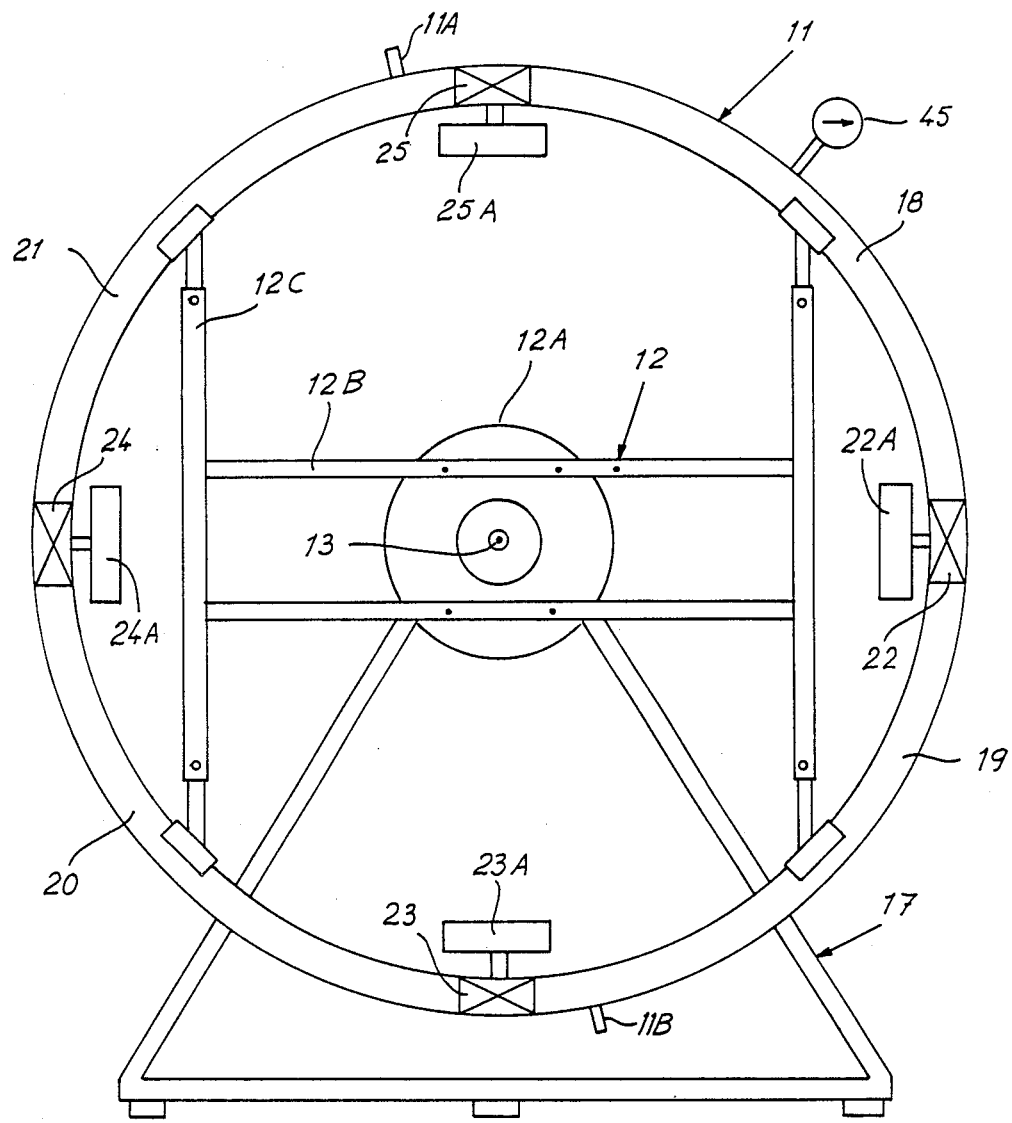
FIG. 1 shows a schematic frontal sketch of the apparatus in accordance with the invention.

The main component in the apparatus, which is illustrated in FIG. 1, is a rotor 11 that includes a group of test chambers or test segments as described below, and which is carried by a hub structure 12 that is installed to rotate on the axle 13 of a motor 14 with a reduction gear 15. The motor 14 is suitably provided with a rotation control (not shown) and is, together with the gear 15, installed on a base 17. The axle 13 is placed generally in a horizontal position. The hub structure 17 comprises a flange 12A with two parallel struts 12B that have telescoping crossbars.

Figure 2:
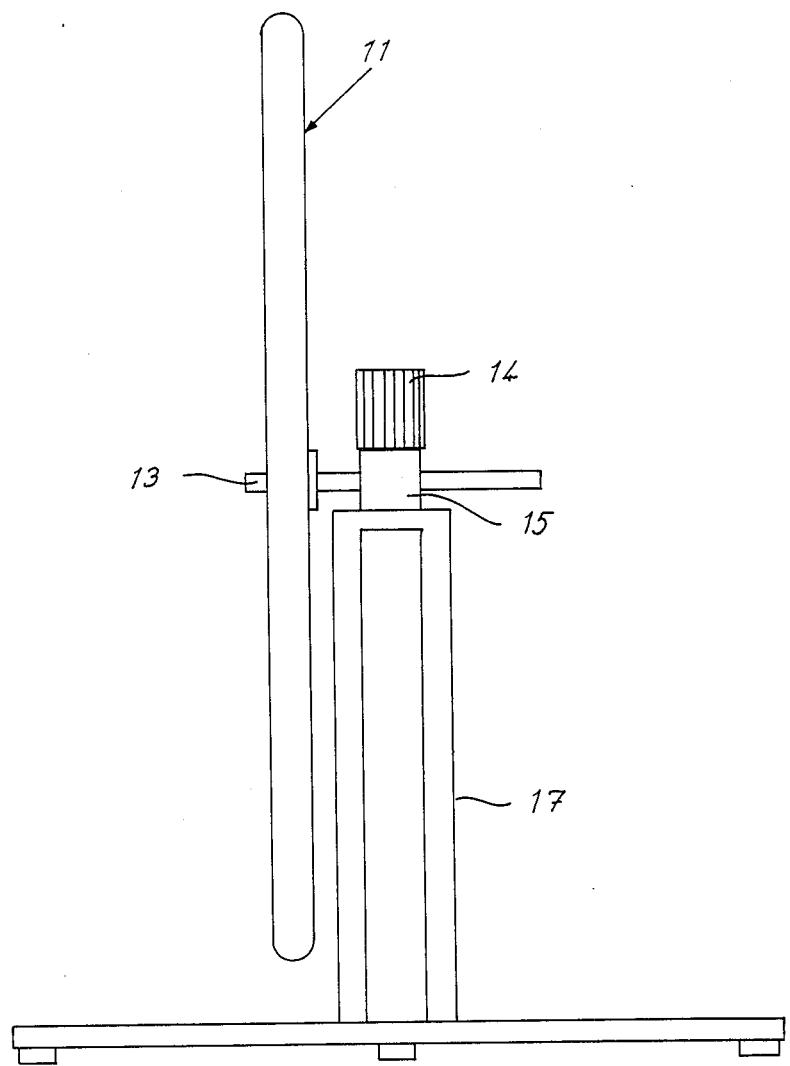
FIG. 2 shows a sketch of the side of the apparatus in FIG. 1.

The rotor 11, which is illustrated in FIGS. 1 and 2, is built up mainly of arced pipe segments and spherical valves, as described in more detail below. With the rotation of the rotor 11 filled partially with the correct liquids and gases, pipe transport at various speeds can be simulated.

Figure 3:
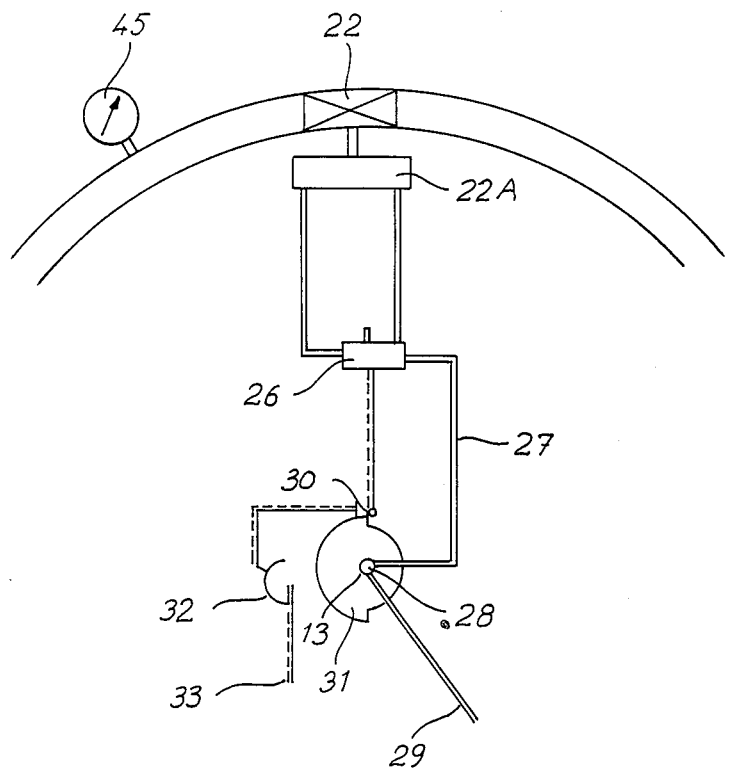
FIG. 3 shows a more detailed extract of FIG. 1.

In the example in FIGS. 1 and 2, the rotor 11 is diveded into four segments, especially of transparent material, 18, 19, 20 and 21, respectively. Valves, especially spherical valves, have been inserted between the segments; between segments 18 and 19, a valve 22 has been placed, between segments 19 and 20, a valve 23 has been placed, between the pair of segments 20 and 21, a valve 24 has been placed, and between segments 21 and 18 a valve 25 has been placed. An actuator can be found for each valve, 22A, 23A, 24A and 25A, respectively. As in the example, it is pneumatically driven, as shown in FIG. 3 and as described below. Valves 22–25 make it possible to guide the flow from one segment to the next according to a certain program and from a control center.

FIG. 3 shows an example of such a valve 22 and its accompanying actuator 22A. The actuator 22A supplies air pressure from a 3-way magnetic valve 26 that feeds through a compressed-air conduit 27, which can be common for all the valves 22–25, and that over a pneumatic swivle 28 placed on the axle 13 is connected to an outer supply line 29.

In order to control the magnetic valve, this is coupled over a switch 30 that is cam-driven from a cam 31 on the axle 13, over a collector ring to an outer supply line 33.

The rotor 11 is provided with an end piece 11A for refilling the test fluid and with an end piece 11B for draining it.

The different segments 18–21 can however, be supplied with various drains (not shown) for the drainage of samples, reconnection of measuring instruments of different types and eventual addition of various elements that are relevent for sample taking.

The illustrated example can be modified in various ways. The total amount of pipe segments can, for example, be less than shown. One or more of the pipe segments can also be exchanged for special test segments. One such test segment intended for use with a stationary rotor is described below.

Figure 4:
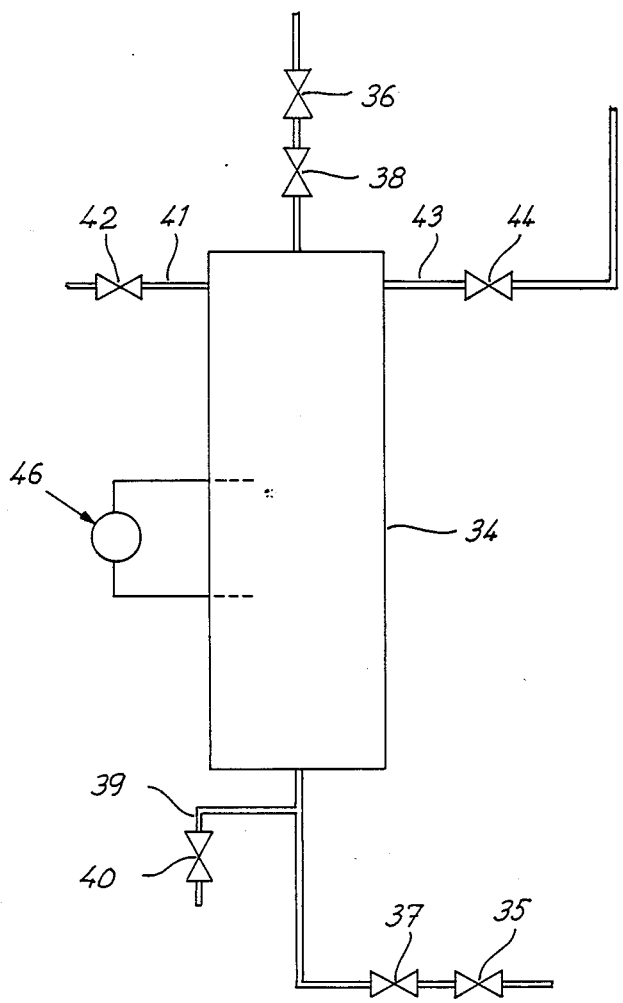
FIG. 4 shows an example of a special segment.

FIG. 4 illustrates a separator tank 34 intended for vertical placement as shown in the figure, and for connection on the underside, over a valve 35 of a pipe segment and over a valve 36, on the top of another. The two valves 35 and 36, have their own chokes 37 and 38 to limit flow. An outlet pipe 39 is also found underneath with a valve 40 for sample taking.

To set the seperator tank under pressure, a supply line 41 with a valve 42 can be found.

In order to remove gas and relieve pressure from the separation tank 34, an outlet pipe 43 with a valve 44 is found at the top that empties out with atmospheric pressure. Reference numbers 46 refer to equipment for level contact and control.

The arrangement in the example can be formulated in detail to take care of special needs for sample taking and treatment of retrieved liquid/gas. This can take place within the parameters of known methods with regard to testing of process fluids, with use of this segment, the rotor stands still and fluids are transferred between the segments by excess pressure during the gas phase.

Dimensioning of the components is chosen according to the amount of space and demands of the similarity to the process. In principle this apparatus can be expanded with pipe segments and spherical valves to full scale. The rotor allows, when it rotates on its axis and is filled with the right liquids/gases, simulation of pipe transport at various speeds. By closing some valves at given positions and opening them at other positions during rotation, it will also be possible to pump the gas through the oil/water and simulate two-phase flow.

We claim:

1. An apparatus for testing fluids, especially for testing physical characteristics or susceptibility to process fluids, comprising:
   a rotor-driven organ with at least one pipe segment that is arched concentrically to the rotational axis, and that can transport the fluid that will be tested and retrieve it during rotation, wherein the rotor-driven organ comprises two or more arched pipe segments and a similar number of valves, each valve being connected between two adjacent arched pipe segments.

2. The apparatus according to claim 1, wherein disposed between two arched pipe segments is a special segment for additional testing of the fluid.

3. The apparatus according to claim 1, wherein that special segment is a separator tank.

4. The apparatus according to claim 1, further comprising two or more actuators, each associated with one of said valves, and a remote-controlled valve, each actuator driving said associated valve, and each said actuator controlled by control pulses from said remote-controlled valve.

* * * * *